(12) United States Patent
Young et al.

(10) Patent No.: US 7,041,055 B2
(45) Date of Patent: May 9, 2006

(54) INSTRUMENTS AND METHODS FOR USE IN LAPAROSCOPIC SURGERY

(75) Inventors: Wayne P. Young, Brewster, NY (US); John I. Shipp, Tullahoma, TN (US); Keith Ratcliff, Newtown, CT (US)

(73) Assignee: Mark LoGuidice, Southport, CT (US)

( * ) Notice: Subject to any disclaimer, the term of this patent is extended or adjusted under 35 U.S.C. 154(b) by 0 days.

(21) Appl. No.: 10/680,973

(22) Filed: Oct. 7, 2003
(Under 37 CFR 1.47)

(65) Prior Publication Data
US 2004/0225192 A1   Nov. 11, 2004

Related U.S. Application Data

(60) Provisional application No. 60/439,759, filed on Jan. 13, 2003, provisional application No. 60/425,523, filed on Nov. 12, 2002, provisional application No. 60/425,522, filed on Nov. 12, 2002, provisional application No. 60/425,506, filed on Nov. 12, 2002, provisional application No. 60/424,755, filed on Nov. 8, 2002, provisional application No. 60/424,754, filed on Nov. 8, 2002, provisional application No. 60/424,752, filed on Nov. 8, 2002, provisional application No. 60/416,665, filed on Oct. 7, 2002.

(51) Int. Cl.
*A61B 1/32* (2006.01)
(52) U.S. Cl. ............ 600/204; 606/198; 604/104
(58) Field of Classification Search ........ 600/204; 606/198; 604/104
See application file for complete search history.

(56) References Cited

U.S. PATENT DOCUMENTS

| | | | |
|---|---|---|---|
| 4,347,846 A | 9/1982 | Dormia |
| 4,611,594 A | 9/1986 | Grayhack et al. |
| 4,807,626 A | 2/1989 | McGirr |
| 5,037,379 A | 8/1991 | Clayman et al. |
| 5,074,867 A | 12/1991 | Wilk |
| 5,143,082 A | 9/1992 | Kindberg et al. |
| 5,147,371 A | 9/1992 | Washington et al. |
| 5,176,687 A | 1/1993 | Hasson et al. |
| 5,190,554 A | 3/1993 | Coddington, III et al. |

(Continued)

FOREIGN PATENT DOCUMENTS

GB    3301    8/1879

*Primary Examiner*—Beverly M. Flanagan
*Assistant Examiner*—Matthew J. Kasztejna
(74) *Attorney, Agent, or Firm*—Martin & Ferraro, LLP

(57) ABSTRACT

An improved surgical dilator extractor is introduced into the abdominal cavity through a trocar cannula and expanded, forming a tissue receiving space, at the distal end. The tissue receiving space is enlarged by passing a grasper through a lumen of the dilator extractor to interact with a guide surface on the interior of dilator extractor to expand a dilator portion having a single leaf beyond the natural resiliency of the leaf. The tissue being extracted is then manipulated into the space with the grasper. The tissue is then removed from the cavity by the surgeon applying a force onto the dilator extractor that insures the elongation of the tissue and temporarily dilates the entry wound to the extent necessary for the tissue to be removed. Alternative embodiments of the surgical dilator extractor and related instrument tool sets and methods for the use thereof also are disclosed.

21 Claims, 10 Drawing Sheets

U.S. PATENT DOCUMENTS

| | | |
|---|---|---|
| 5,190,561 A | 3/1993 | Graber |
| 5,192,284 A | 3/1993 | Pleatman |
| 5,281,230 A | 1/1994 | Heidmueller |
| 5,312,417 A | 5/1994 | Wilk |
| 5,320,627 A | 6/1994 | Sorensen et al. |
| 5,341,815 A | 8/1994 | Cofone et al. |
| 5,351,680 A | 10/1994 | Jung |
| 5,370,647 A | 12/1994 | Graber et al. |
| 5,431,676 A | 7/1995 | Dubrul et al. |
| 5,465,731 A | 11/1995 | Bell et al. |
| 5,480,404 A | 1/1996 | Kammerer et al. |
| 5,486,183 A | 1/1996 | Middleman et al. |
| 5,527,274 A | 6/1996 | Zakko |
| 5,630,805 A | 5/1997 | Ternamian |
| 5,643,227 A | 7/1997 | Stevens |
| 5,643,282 A | 7/1997 | Kieturakis |
| 5,643,313 A | 7/1997 | Levin |
| 5,647,372 A | 7/1997 | Tovey et al. |
| 5,681,324 A | 10/1997 | Kammerer et al. |
| 5,814,058 A | 9/1998 | Carlson et al. |
| 5,827,319 A | 10/1998 | Carlson et al. |
| 5,836,913 A | 11/1998 | Orth et al. |
| 5,843,017 A | 12/1998 | Yoon |
| 5,853,399 A | 12/1998 | Sasaki |
| 5,906,622 A | 5/1999 | Lippitt et al. |
| 5,908,435 A | 6/1999 | Samuels |
| 5,924,175 A | 7/1999 | Lippitt et al. |
| 5,944,728 A | 8/1999 | Bates |
| 5,971,995 A | 10/1999 | Rousseau |
| 6,036,708 A | 3/2000 | Sciver |
| 6,080,174 A | 6/2000 | Dubrul et al. |
| 6,099,550 A | 8/2000 | Yoon |
| 6,162,235 A | 12/2000 | Vaitekunas |
| 6,350,267 B1 | 2/2002 | Stefanchik |
| 6,383,195 B1 | 5/2002 | Richard |
| 6,800,084 B1 * | 10/2004 | Davison et al. ............ 606/198 |
| 2002/0068943 A1 | 6/2002 | Chu et al. |
| 2002/0137988 A1 * | 9/2002 | Shipp et al. ................ 600/204 |

* cited by examiner

INSTRUMENTS AND METHODS FOR USE IN LAPAROSCOPIC SURGERY

RELATED APPLICATIONS

This application claims the benefit of U.S. Provisional Application No. 60/416,665, filed Oct. 7, 2002; U.S. Provisional Application Nos. 60/424,752; 60/424,754; and 60/424,755, each filed Nov. 8, 2002; U.S. provisional Application Nos. 60/425,506; 60/425,522; and 60/425,523, each filed Nov. 12, 2002; and U.S. Provisional Application No. 60/439,759, filed Jan. 13, 2003, all of which are incorporated by reference herein.

BACKGROUND OF THE INVENTION

The present invention relates generally to mechanical devices and methods used in laparoscopic surgical procedures to remove organs and excised tissue from internal body cavities.

It will be appreciated by those skilled in the art that the use of bags or pouches to remove organs and large tissue specimen during laparoscopic surgical procedures is well known. As described, for example, in U.S. Pat. No. 5,147,371 a pouch is introduced into the abdominal cavity for retrieving gallstones and tissue. The bag is opened and closed using a wire loop as a drawstring. In U.S. Pat. No. 5,192,284 an expandable bag is inserted into the abdominal cavity through a trocar cannula. The bag described in the '284 patent is made of a memory material that is rigid enough to support itself. The bag expands and remains open when it is inserted into the abdominal cavity through the cannula. U.S. Pat. No. 5,480,404 describes a pouch for extracting tissue that is opened and closed by a ratchet mechanism. U.S. Pat. No. 5,341,815 employs shape memory effect metal to open the bag upon insertion through a trocar. U.S. Pat. Nos. 5,681,324 and 5,971,995 describe similar bags and pouches.

The pouches described in these patents are useful in containing any bile or gallstones that might otherwise spill into the abdominal cavity during extraction of a torn gallbladder. These types of devices, however, suffer from at least three problems. Since such devices are closed on the distal end, air inside the enclosure tends to balloon the pouches or bags during the extraction process thereby increasing the size or not allowing a full collapse of a bag as it is removed from the wound. Additionally, when the tissue is larger than the wound size, it is forced to the bottom of the bag as the radial force of the wound acts on the tissue during extraction. This also increases the size to which the wound must be dilated for removal of the tissue. Tapering the bags toward the distal end helps somewhat to lessen this effect, but the result is not optimal and does not fully address the problem of air trapped in the bag. Finally, the work required to remove a gall bladder is equal to the extraction force times the distance over which the force is required to act plus any heat generated by friction. For example the work required to remove a bagged gallbladder with a 30 mm diameter stone is the same as the work required to extract the same gall bladder that is contained in a rigid shallow cone with a maximum diameter of 30 mm (neglecting friction differences). The peak force for removal is much higher, however, for the bagged gallbladder since the force is required to act over a much smaller distance. Since it is desirable to minimize the forces required to extract a gallbladder owing to material and human limitations, the gallbladder should be, by way of example only, contained in a rigid shallow cone rather than a flexible bag.

Since the goal of laparoscopic surgery is to become less invasive by using smaller entry wounds, the prior art is of limited value for removing large specimens through, for example, 5 mm wounds. When the user pulls on the bag in an attempt to remove it through a small trocar entry wound, the specimen is forced to the bottom of the bag by the radial forces exerted by the abdominal tissue or by the forces exerted on the bag from the cannula, thus creating a large lump that is often incapable of passing through the wound without tearing the bag. The use of this type of extraction bag in these cases often requires de-bulking of the specimen so that the bagged specimen pieces are of such a size that the bag can be extracted through the trocar entry wound, typically 10–12 mm. This is a time consuming process that is not always successful since, for example, large stones may be inside a gallbladder and the process usually necessitates the pathologic examination of the tissue specimen. As an alternative to de-bulking, the wound size may be increased with a scalpel to allow the extraction. This approach, however, lessons the advantage of the laparoscopic surgery. Additionally, these types of extraction bags add undue complexity to the procedure since they require the use of two ports, one for the bag and a second for a grasper to retrieve the tissue and put it into the bag.

U.S. Pat. Nos. 5,190,561 and 5,370,647 to Graber disclose several embodiments of laparoscopic extraction devices that allow a grasper to be inserted into the center of an extractor device so that tissue can be more easily manipulated into the inside of the extractor. In each of the embodiments the extractor is introduced into the abdominal cavity through a specially designed trocar cannula equipped with setscrews to lock the extractor to the trocar cannula. Upon exiting the distal end of the cannula, the distal end of the extractor expands, much like an umbrella. A grasper is then introduced into the abdominal cavity through a lumen in the extractor. The specimen is grasped and pulled into the expanded open distal end of the extractor, a cone-shaped device. The grasper is then locked to the cannula using the setscrews. The proximal end of the extractor is equipped with a handle, which is used to pull the extractor and the tissue through the cannula. As the handle is pulled upward " . . . the enveloping means collapses around the tissue and returns to its pre-deployment." The enveloping means of Graber '647 is relied on to compress the tissue to a size that allows it to be drawn into a hollow tubular shroud 610 (see FIG. 13 of Graber '647). Thus, the device is not optimally designed to deal with a tissue specimen that will not compress to a point so that it can be drawn into the shroud.

The extractor of Graber '647 also has several other disadvantages. The Graber '647 device is ill-suited for use with standard trocars because it utilizes setscrews, which are not generally available on trocars in current use, to lock it to the trocar. The Graber '647 device also utilizes an expensive locking mechanism to lock the grasper to the extractor. In addition, most abdominal laparoscopic procedures are performed with the abdominal cavity insufflated with carbon dioxide. The lumen in the extractor of Graber '647 has no provision for sealing and thus when the extractor is placed through the seal of the trocar, the abdomen will loose its carbon dioxide pressure through the lumen of the extractor.

The Graber '647 device is removed from the body cavity by an exertion force on the handle of the device. This unduly places rotational and shear forces on the extractor-grasper lever lock and the extractor-trocar setscrews because of the vigorous rotational manipulation required to remove it from the abdominal wall.

One of the extractor covers disclosed in the Graber '647 patent is made from "a sturdy waterproof, stain resistant fabric such as treated sailcloth or duck cloth." These materials are thick, bulky, and generally not suited for extractors for use with less invasive trocar cannula such as 5 mm and smaller devices. In particular, such covers require multiple folds in order for the extractor to pass through a small-bore cannula. FIG. 24 of the Graber '647 patent discloses a thin "baggie," however, it requires thick leaves 608 and a plunger rod 606 to compress the tissue. The combination and thickness of these features is unduly complicating and makes the Graber device ill-suited for small cannulas.

The embodiment disclosed in FIG. 12 of the Graber '647 patent teaches the use of a flexible, waterproof web material with an opening mouth so that tissue can enter the rib portion 510. While this embodiment partially solves the spillage problem it unduly complicates manipulating the tissue inside the extractor and is overly complex in that the extractor cover and the spillage compartment are made of two separate pieces which must be joined by sewing, heat treating, or welding.

Graber also discloses a multi-leaf rigid cover that is pinned to a hollow elongated shank. The leaves are rolled into a generally cylindrical shape inside the shank in an un-deployed state and expanded into a generally conical shape in a deployed state. An extraction dilation device having a single leaf is desirable owing to its simplicity. Graber does not teach a method or mechanism for attaching a single leaf to the shank since fixedly pinning a single-leaf sheet to the shank results in buckling of the cone when attempting to roll it into a generally cylindrical shape for insertion within a tube.

Laparoscopic removal of the gallbladder has, heretofore, entailed the use of four entry cannula, typically two of which are 10 to 12 mm in diameter and two of which are 5 mm in diameter. The two 5 mm ports are used to accept instruments such as scissors, graspers, electro-surgery probes, and suction/irrigation devices. The 10 to 12 mm ports are employed to allow the use of instruments such as a 10 mm endoscope attached to a camera for viewing the surgical field or a clip applier for ligating vessels and ducts, and to permit the removal of a gallbladder following its excision.

In an effort to make the procedure less invasive, 5 mm clip appliers have been developed, such as described by Shipp et al. in U.S. Pat. No. 5,858,018, the disclosure of which is incorporated by reference herein. The 5 mm clip applier allows the conversion of one of the two 10 to 12 mm ports to a third 5 mm port. The remaining 10 to 12 mm port prior to this invention has been required to accept 10 mm endoscopes and to permit the removal of the gallbladder, usually through the umbilicus port site. New bright 5 mm endoscopes coupled with more sensitive cameras have been developed that are quite acceptable substitutes for the prior art camera systems. These developments leave gallbladder removal through a 5 mm or smaller port as the last obstacle to the full conversion of the process to four much less invasive 5 mm ports. The conversion from two 10 to 12 mm trocars and two 5 mm trocars to four 5 mm trocars lowers the total entry wound area by 50 percent, which greatly reduces bleeding and post surgery incisional herniation at the wound sites.

What is needed then is a simple, inexpensive device and an easy to use method for rapid removal of tissue, such as a gallbladder, from a wound site that has an opening size that is smaller than the size of the specimen and does not require substantial secondary operations such as grinding the specimen into smaller pieces or significantly enlarging the wound size. Also needed is a simple, rigid single-leaf dilator extractor that is attached to a hollow shank such that the leaf may easily be rolled into a shape exhibiting a minimal diameter for insertion into a small trocar cannula, for example, 5 mm. Preferably, the deployed dilator extractor is sufficiently rigid so as to provide a smooth, shallow angled cone shape so that the force required to remove the tissue is minimized. Preferably, the dilator extractor is self-deployable to a sufficient base diameter upon exiting the cannula, even after prolonged storage in a rolled-up or un-deployed state.

SUMMARY OF THE INVENTION

The present invention in one embodiment is directed to an expandable dilator extractor that expands upon entry into the abdominal cavity for acceptance of a tissue specimen using a grasper to pull the specimen into the interior of the dilator extractor. The construction of the dilator is such that when a surgeon places an upward force, away from the surface of the abdomen on the deployed dilator, it minimizes the cross section of the tissue by closing a cone about the specimen, and thus minimizes the wound dilation requirement. The resulting elongated conical shape forces the trocar puncture wound to expand to allow the larger specimen to be extracted with a minimum of tearing or otherwise permanently enlarging the wound. The cone angle is minimized to provide the maximum mechanical advantage and thus minimizes the force necessary for the surgeon to exert on the device for extraction.

A preferred embodiment of the extractor includes a body having a leading end, a trailing end, a lumen between the leading and trailing ends, and a mid-longitudinal axis passing through the lumen of the body. The extractor also includes a dilator at the leading end of the body that is movable between an unexpanded position and an expanded position. The dilator has a single leaf adapted to be rolled at least in part around the mid-longitudinal axis of the extractor. The dilator has a guide surface configured to engage an instrument inserted through the lumen. The guide surface is adapted to move at least a portion of the dilator away from the mid-longitudinal axis of the extractor upon engagement with the instrument.

Another preferred embodiment of the extractor includes a body having a leading end, a trailing end, a lumen between said leading and trailing ends, and a mid-longitudinal axis passing through the lumen of the body. The extractor also includes a dilator at the leading end of the body that is movable between an unexpanded position and an expanded position.

The extractor also includes a collar that has an opening and is movable relative to the body along the mid-longitudinal axis of the extractor. The body is adapted to pass through the opening in the collar. A retainer is attached to the collar. The retainer is adapted to retain the dilator in the unexpanded position until the body passes through the opening in the collar to move the dilator towards the expanded position.

Another embodiment of the present invention is also directed to a surgical tissue collection bag for removing tissue from an animal or human body cavity. The bag includes a top, a bottom, and at least one side between the top and the bottom. The top has an opening with a perimeter. The bag also includes a resilient expansion member that is movable between an unexpanded position and an expanded position. The expansion member is positioned around at least a portion of the opening. The expansion member is biased toward the expanded position.

Yet another embodiment of the present invention also is directed to a method for removal of excised tissue with minimal force. The method includes providing an extractor having a dilator movable between an unexpanded position and an expanded position. The dilator is made of a material that is biased at least in part toward the expanded position. The extractor is inserted through a cannula and at least in part into the body cavity. The dilator is released to move at least in part toward the expanded position. A portion of the extractor is engaged with an instrument to further move the dilator toward the expanded position. Tissue is removed from the body cavity.

In another embodiment the present invention includes a method of removing tissue by placing the tissue in a leak-proof bag and inserting the bagged specimen into a deployed dilator extractor prior to extraction.

DESCRIPTION OF THE PREFERRED EMBODIMENTS

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

Figure 1:
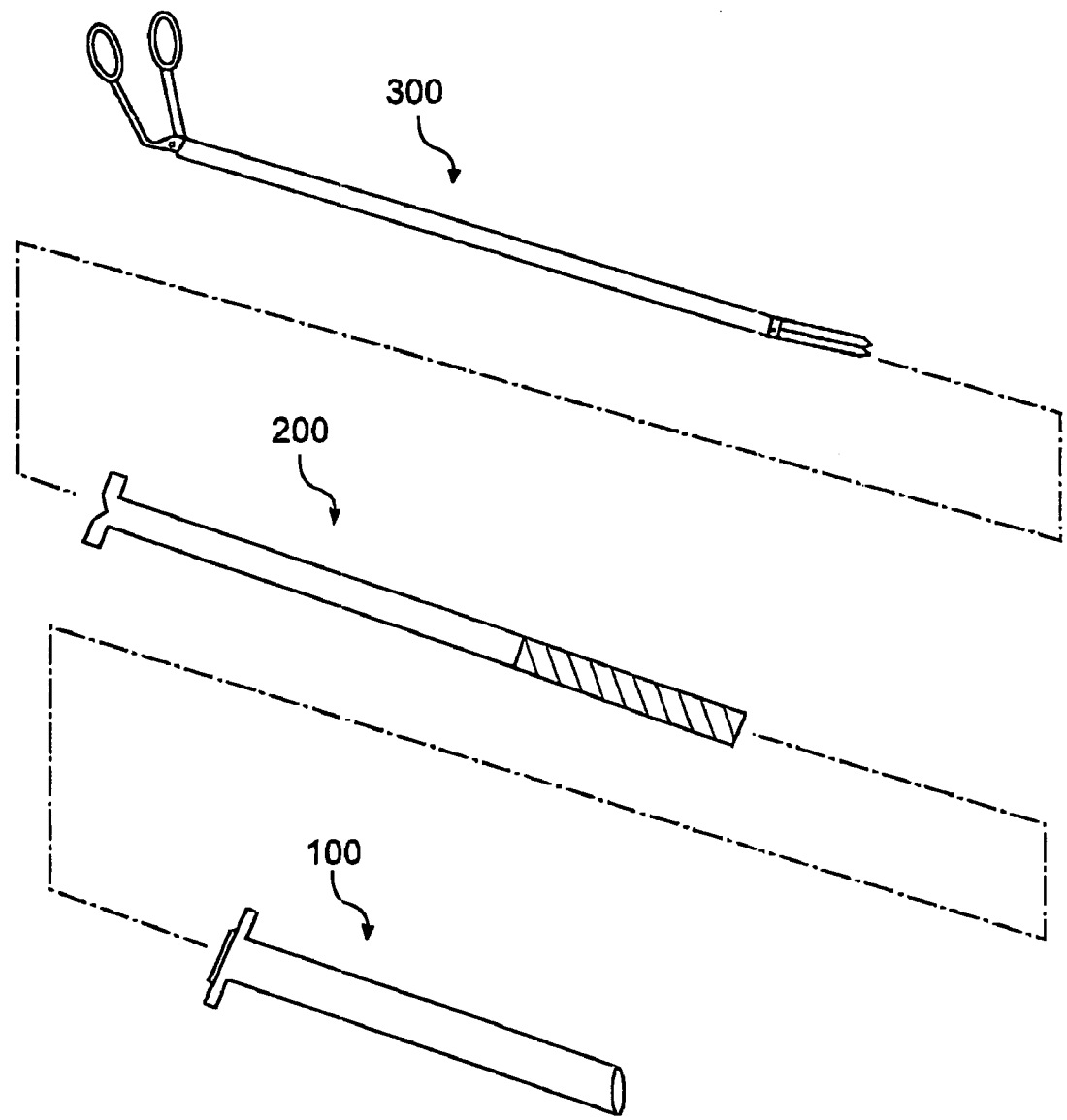
FIG. 1 is a diagrammatic view of a grasper, a dilator extractor, and a cannula in accordance with one embodiment of the present invention.

FIG. 1 shows a tool set having a cannula 100, a dilator extractor 200, and a grasper 300. Grasper 300 is insertable in dilator extractor 200, which in turn is insertable in cannula 100 to form a multi-coaxial assembly for use in laparoscopic surgery. An example of a tool set suitable for use in laparoscopic surgery is described in co-pending U.S. application Ser. No. 10/047,122, filed Jan. 15, 2002, which is incorporated herein by reference.

Referring to FIGS. 2–5 and 8, dilator extractor 200 is inserted into a pressurized abdominal cavity 60 through the abdominal wall of a patient. Dilator extractor 200 enters through valve 102 at trailing end 106 of cannula 100.

Dilator extractor 200 includes a body 202 having a leading end 204, a trailing end 206, a mid-longitudinal axis L, and a lumen 208. Body 202 includes a dilator 210 at leading end 204 that is movable between an unexpanded position, shown in FIG. 2, and an expanded position, shown in FIG. 8. Trailing end 206 preferably includes a depth-limiting protrusion in the form of shoulder 207. Shoulder 207 is adapted to limit the deployment expansion of the cone of dilator 210.

When the trailing end portion of dilator 210 clears leading end 104 of cannula 100, dilator 210 expands to the expanded position preferably owing in part to the natural tendency of dilator cone 216 to unroll, thus forming a truncated conical-shaped tissue receiving space 214, enclosed by dilator cone 216.

Figure 2:
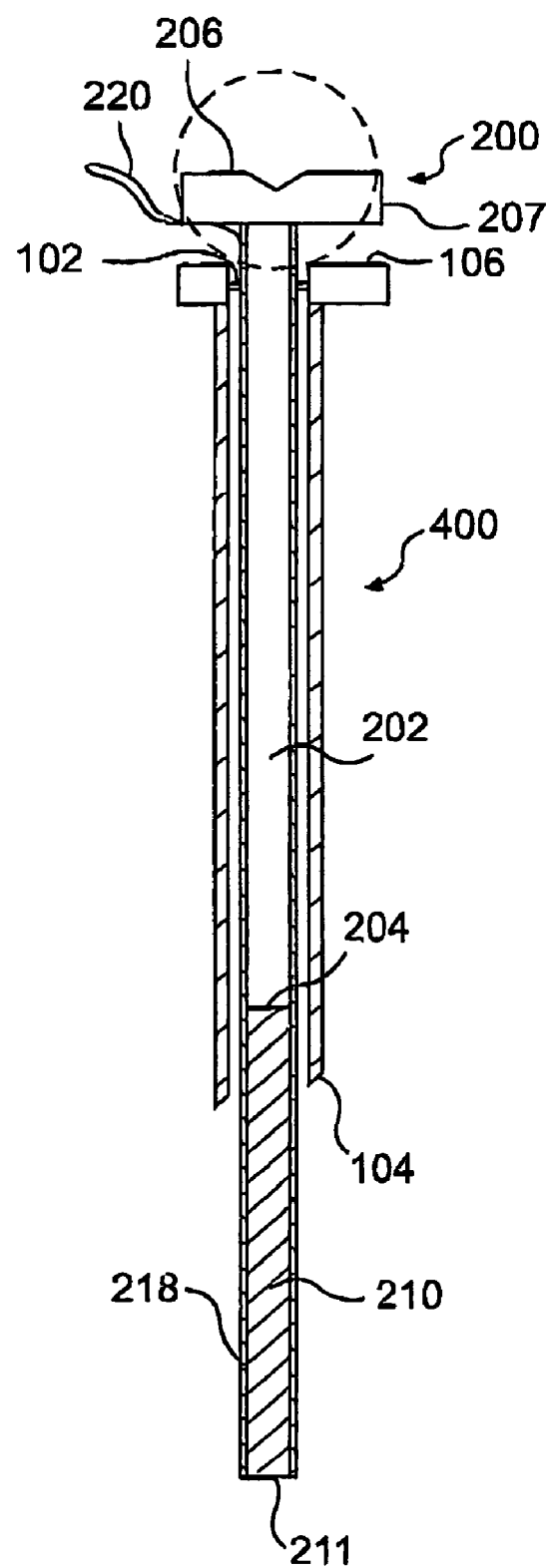
FIG. 2 is a partial side sectional view of the dilator extractor of FIG. 1 inserted in the cannula of FIG. 1.

FIG. 2 shows dilator extractor 200 before dilator 210 clears leading end 104 of cannula 100. Dilator 210 may be preserved in the unexpanded position because of the inner diameter of cannula 100. Dilator cone 216 is preferably wrapped upon itself to allow the passage of dilator extractor 200 in the unexpanded position through cannula 100.

In a preferred embodiment, retainer 218 maintains dilator extractor 200 in the unexpanded state. One suitable retainer is straw-shaped and encircles dilator 210. Retainer 218 extends toward trailing end 206 of dilator extractor 200 terminating into a graspable surface grip 220 proximate trailing end 206. The composition of retainer 218 is such that it is strong enough to restrain the spring forces of dilator 210, yet an upward force on graspable surface grip 220 will cause retainer 218 to peel open allowing dilator 210 to expand. By way of example, a suitable strength welded seam in a polyurethane film can accomplish such a peeling feature.

Figure 3:
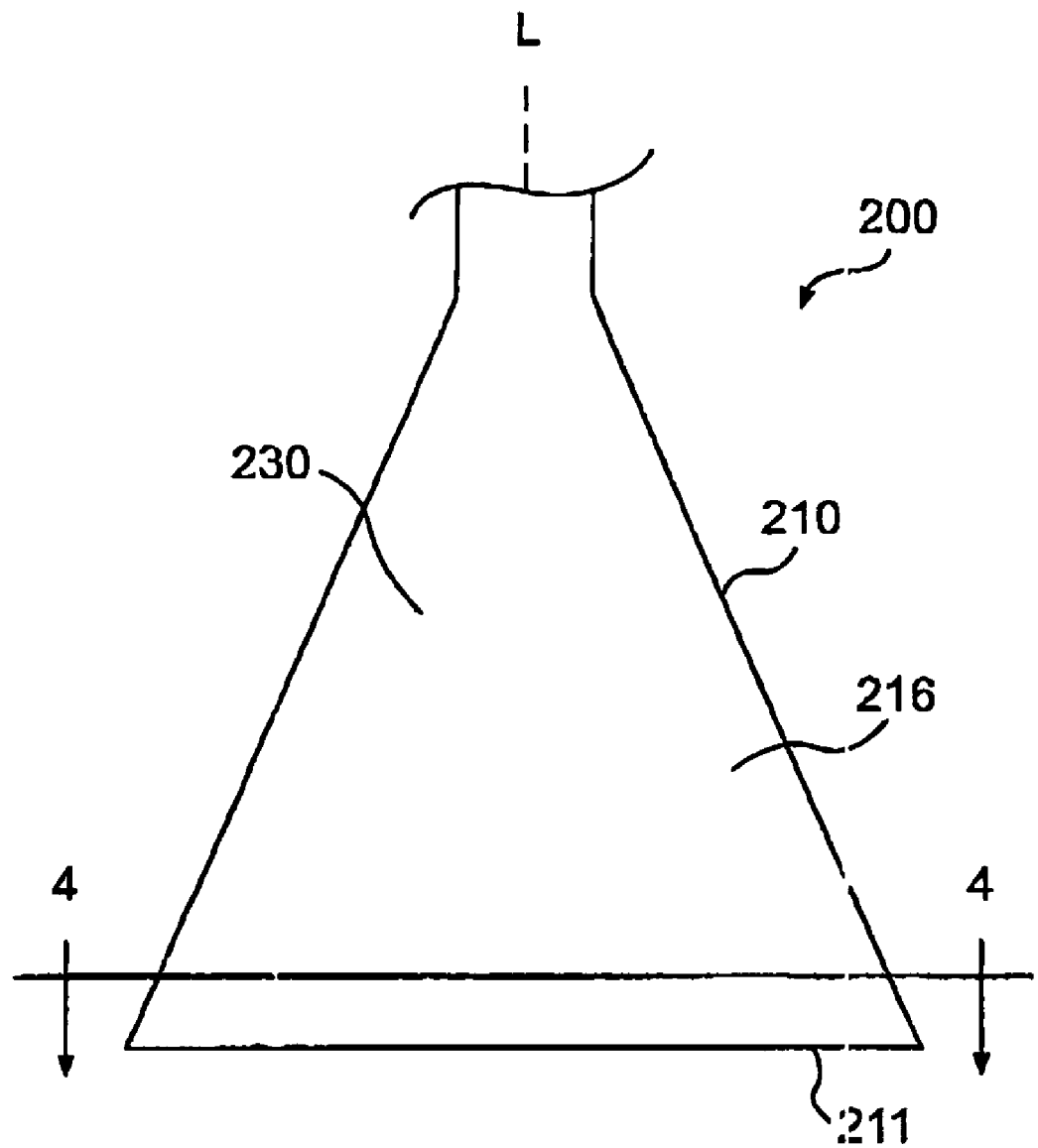
FIG. 3 is a partial side elevation view of the leading end of the dilator extractor of FIG. 1 in an expanded position.
Figure 4:
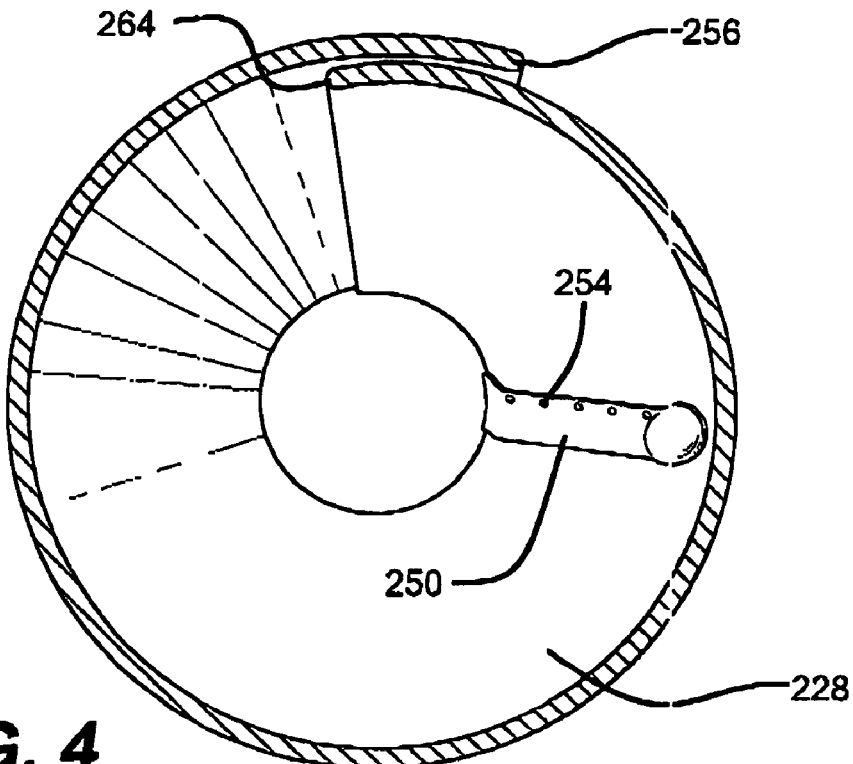
FIG. 4 is a bottom plan view along line 4—4 of FIG. 3.
Figure 5:
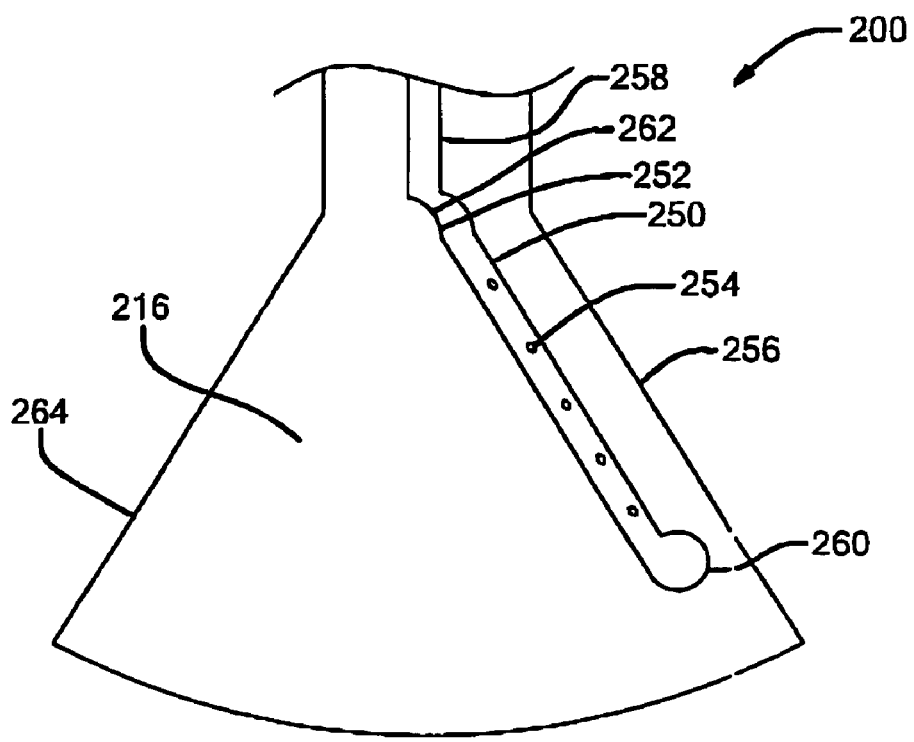
FIG. 5 is a sheet metal layout of the dilator extractor of FIG. 1 prior to being rolled and formed into a conical shape.

In one preferred embodiment a conical section 216 of dilator 210, as best shown in FIGS. 3–5, is preferably made of a laminated, rigid, material that will allow it to be rolled and contained in cannula 100 prior to expansion of dilator 210 of dilator extractor 200. Exemplary materials include plastic and metal, such as series 300 stainless steel. Conical section 216 is preferable a single leaf. A single leaf is advantageous for increasing the strength of conical section 216 as well as reducing the number of moving parts during the expansion of dilator 210.

Conical section 216 includes an inner surface 228 and an outer surface 230. Outer surface 230 of dilator cone 216 preferably has a low coefficient of friction, such as a PTFE (polytetrafluoroethylene) coating. Inner surface 228 preferably has high coefficient of friction, such as a sand blasted or otherwise roughened surface. It will be appreciated by those skilled in the art that other materials are suitable for providing a coefficient of friction that is higher on inner surface 228 than outer surface 230 and are within the scope of the present invention. Preferably, the coefficient of friction of inner surface 228 is in the range of 0.5 to 1.0. The low friction outer surface 230 of conical section 216 minimizes the force required for extraction while the high friction inner surface 228 provides a gripping force on the tissue surface area and thereby minimizes the force transferred to the grasper/tissue interface during the dilation extraction process. The dilation forces acting on the dilator require that the tensile strength of conical section 216 is adequate to withstand the friction force exerted by the tissue on inner surface 228. While a differential coefficient of friction is preferred, the present invention is not so limited. For example, inner surface 228 may be smooth.

Figure 8:
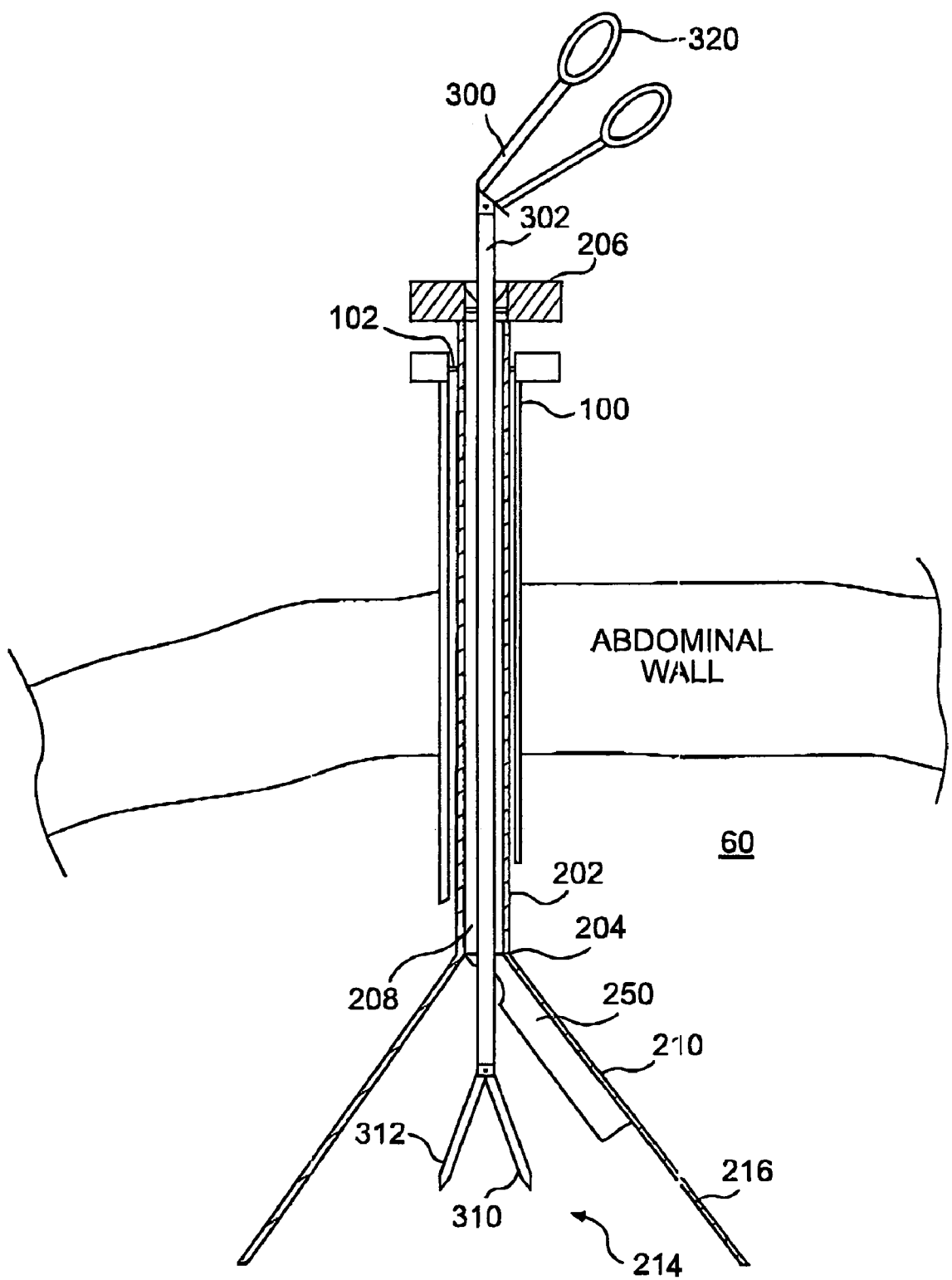
FIG. 8 is a side elevation view of a grasper, dilator extractor, and cannula inserted in the abdominal wall of a patient, the grasper being inserted in the dilator extractor, the dilator extractor being inserted in the cannula, the dilator extractor and cannula being shown in cross section with the dilator extractor in the expanded position.

FIGS. 3 and 4 show dilator 210 in the expanded position. Once dilator 210 of dilator extractor 200 is in the expanded position as depicted in FIG. 8, grasper 300, in a preferred embodiment, is inserted through channel or lumen 208, into tissue space 214, and into cavity 60.

FIG. 5 shows sheet metal layout of the present invention having conical section 216 of a preferably thin, rigid material to which shank 250 is spot welded at locations 254 along a first edge 256 of conical section 216. Shank 250 has a proximal end 258 and a distal end 260. Shank 250 preferably includes a cut-out portion 262 near proximal end of dilator 210. Cut-out portion 262 preferably has a guide surface 252 configured to contact and interact with grasper 300 to provide force to bend shank 250 so that grasper 300 is deployed through the center of conical section 216. Cut-out portion 262 assists in permitting shank 250 to bend when dilator 210 moves from the un-deployed position to the deployed position while centering conical section 216 along mid-longitudinal axis L of dilator 200. It is understood that guide surface 252 may be shaped in a variety of ways while still remaining within the scope of the present invention. For example, guide surface 252 may be a notch, indentation, projection, or other type of surface irregularity or deviation configured to interact with an instrument inserted through body 202. It is further understood that instead of a shank, the guide surface may be formed integral with the interior of dilator 210.

Distal end 260 of shank 250 is configured as a key-way to interact with a key used to roll dilator 210 into a generally cylindrical shape so that first and second edges 256, 264 overlap. Distal end 260 may be angled from the interior of dilator 210 for easier access with the key.

Figure 6:
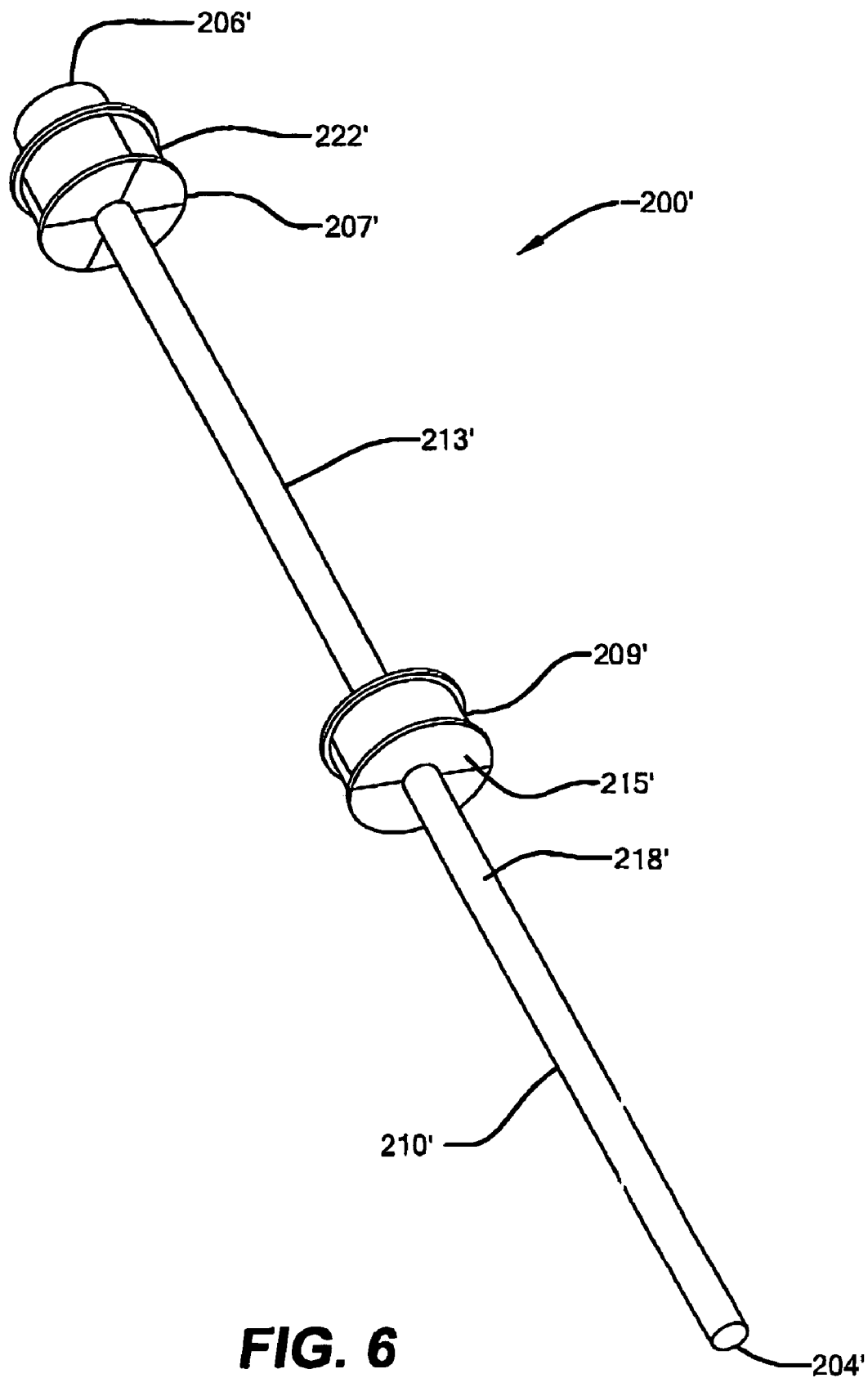
FIG. 6 is a perspective view of a dilator extractor in accordance with another preferred embodiment of the present invention.

FIG. 6 shows a dilator extractor 200' in accordance with another preferred embodiment of the present invention. Dilator extractor 200' has a leading end 204' and a trailing end 206'. Leading end 204' includes a dilator 210' with a retainer 218' wrapped therearound. Trailing end 206' includes a shoulder 207', a knob 222', and a portion 213'. Located between leading and trailing ends 204', 206' is a ring or collar 209'. Retainer 218' is preferably attached to ring 209' at bottom surface 215' of ring 209'.

Dilator extractor 200' is configured so that retainer 218' is removed during the insertion of dilator extractor 200' into cannula 100. For example, while inserting dilator extractor 200' into cannula 100, bottom surface 215' of ring 209' comes into contact with trailing end 106 of cannula 100. Continued insertion of dilator extractor 200' into cannula 100 causes trailing end 206' of dilator extractor 200' to move toward ring 209'. Because retainer 218' remains attached at bottom surface 215', retainer 218' is removed from dilator 210' as dilator 210' is further inserted into the cannula. Once dilator 210' clears leading end 104 of cannula 100, dilator 210' moves into a deployed position. Trailing end 206' of dilator extractor 200' continues moving towards ring 209' until it contacts shoulder 207'. Shoulder 207' also acts to limit the depth of insertion of dilator extractor 200' into cannula 100. Shaft 213' has an attached cone that is pushed through retainer 218' so as to fully deploy the cone when shoulder 207' of knob 222' meets ring 209'. Cannula 100 is stationary. The cone is welded to outside of shaft 213'. It is understood that any of the embodiments disclosed herein may include a configuration having a shoulder at the trailing end of the dilator extractor and a collar with a retainer attached thereto so that as the body is pushed through the retainer, the shoulder of the trailing end of the dilator extractor contacts the collar and the cone deploys.

As shown in FIG. 8, trailing end 206 preferably includes first and second seals. The first seal preferably forms a duckbill "V" shaped valve made of a resilient material that forms a seal when no instrument is inserted into lumen 208. The second seal is preferably formed of a resilient material containing a through hole in its center. The through hole is preferably smaller than the maximum cross sectional dimension of the instrument that the through hole is adapted to receive and forms a seal when the instrument is inserted into lumen 208. For example, both seals may preferably be configured to permit the passage of grasper 300 therethrough while inhibiting a loss of pressure from within the patient. It is appreciated that more than or less than two seals may be used without departing from the scope of the present invention.

Figure 9:
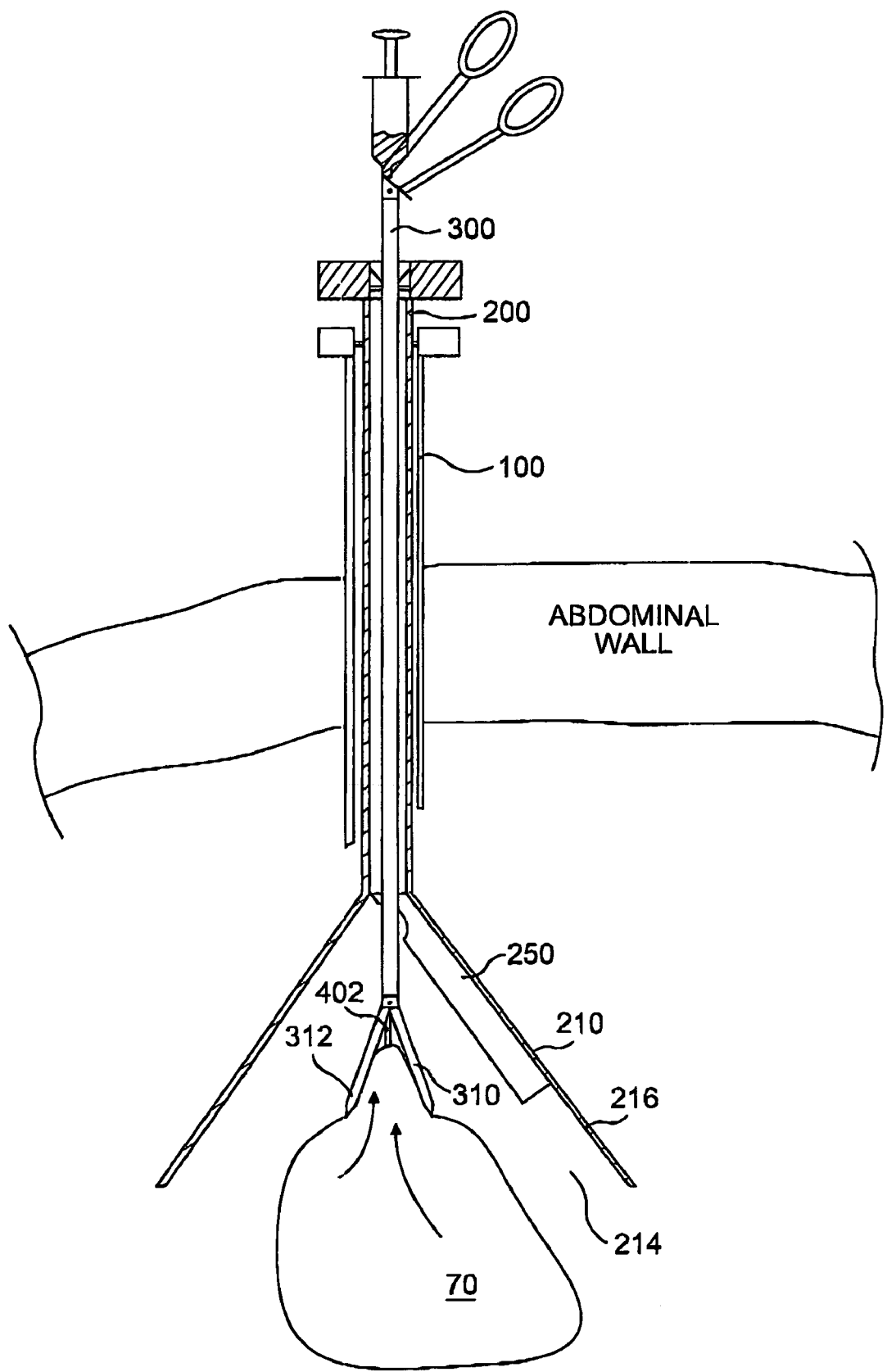
FIG. 9 is a side elevation view of a syringe, grasper, dilator extractor, and cannula inserted in the abdominal wall of a patient, the grasper being inserted in the dilator extractor, the dilator extractor being inserted in the cannula, the dilator extractor and cannula being shown in cross section with a tissue specimen being aspirated in accordance with the instrumentation and method of the present invention.

As shown in FIG. 9, excised tissue 70 is grasped by jaws 310, 312 of grasper 300 and pulled inside conical tissue space 214. Once tissue 70 is inside conical tissue space 214, the entire assembly (grasper 300, dilator extractor 200, trocar cannula 100, and tissue 70) is ready for extraction.

Figure 10:
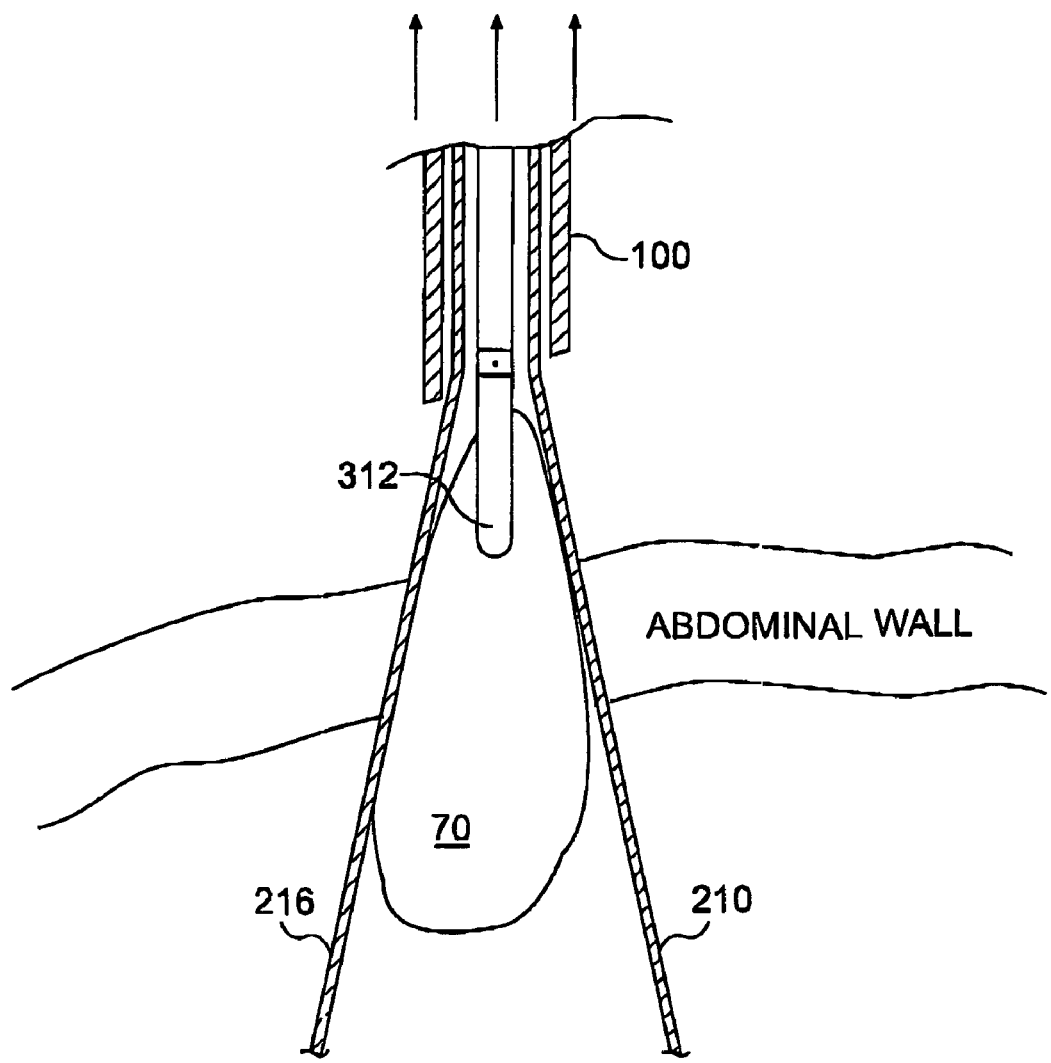
FIG. 10 is a partial side elevation view of the grasper, dilator extractor, and cannula of FIG. 9 being withdrawn from the abdominal cavity with the tissue specimen in accordance with the instrumentation and method of the present invention.

In instances where the tissue specimen is larger than the inside diameter of cannula 100, such as would usually be the case for a gallbladder specimen with a 5 mm cannula for example, dilator 210 will close somewhat under the influence of the upward force of the surgeon until the tissue resilient forces offset the radial forces asserted by the abdominal wall. At this point conical tissue space 214 of dilator extractor 200 will no longer contract and grasper 300, dilator extractor 200, and cannula 100 will be locked together in a more or less rigid fashion. This condition is depicted in FIG. 10. Dilator extractor 200 is constructed in such a manner that application of additional force causes the wedge shape of dilator 210 to begin to increase or dilate the trocar wound in the abdominal wall as the surgeon applies more and more upward force. The larger the specimen, the larger the force necessary to dilate the abdominal wall wound to a size large enough to allow the entire assembly to be removed. The tensile strength of dilator 210 must be adequate to withstand the extraction force. The shape of the trocar puncture wound is important to insure against tearing of the entry wound. A slit entry wound rather than star-shaped entry wound is preferred.

Grasper 300, as shown in FIGS. 1 and 8, has a shaft 302 having a leading end, a trailing end, and a lumen through the center of shaft 302 that can be occupied by a needle of a syringe device. Shaft 302 includes jaws 310, 312 at the leading end for grasping tissue therebetween. As will be appreciated by those of skill in the art, grasper 300 may be adapted to have more than two jaws. For example, a third jaw maybe used to provide a third grasping surface for grasping the tissue. It will be further appreciated that other jaw configurations are possible and within the scope of the present invention. Jaws 310, 312 may have a smooth grasping surface, or may have ridges.

Shaft 302 preferably has a length in the range of 15 cm to 35 cm and an outside maximum cross sectional dimension of less than 5 mm. The lumen of shaft 302 preferably has an inside maximum cross sectional dimension in the range of 1 mm to 4 mm.

As shown in FIG. 8, the trailing end of grasper 300 includes a pair of handles 320 for moving jaws 310, 312 relative to one another. The trailing end also preferably includes first and second seals. The first seal preferably forms a duckbill "V" shaped valve made of a resilient material that forms a seal when no instrument is inserted into the lumen. The second seal is preferably formed of a resilient material containing a through hole in its center. The through hole is preferably smaller than the maximum cross sectional dimension of the instrument that the through hole is adapted to receive and forms a seal when the instrument is inserted into the lumen. For example, both seals may preferably be configured to permit the passage of a needle therethrough while inhibiting a loss of pressure from within the patient. It is appreciated that more than or less than two seals may be used without departing from the scope of the present invention.

The trailing end preferably includes a depth-limiting protrusion for limiting the depth of insertion of grasper 300 into the cavity. The depth-limiting protrusion may be formed as a shoulder, or may form a part of handles 320.

Figure 11:
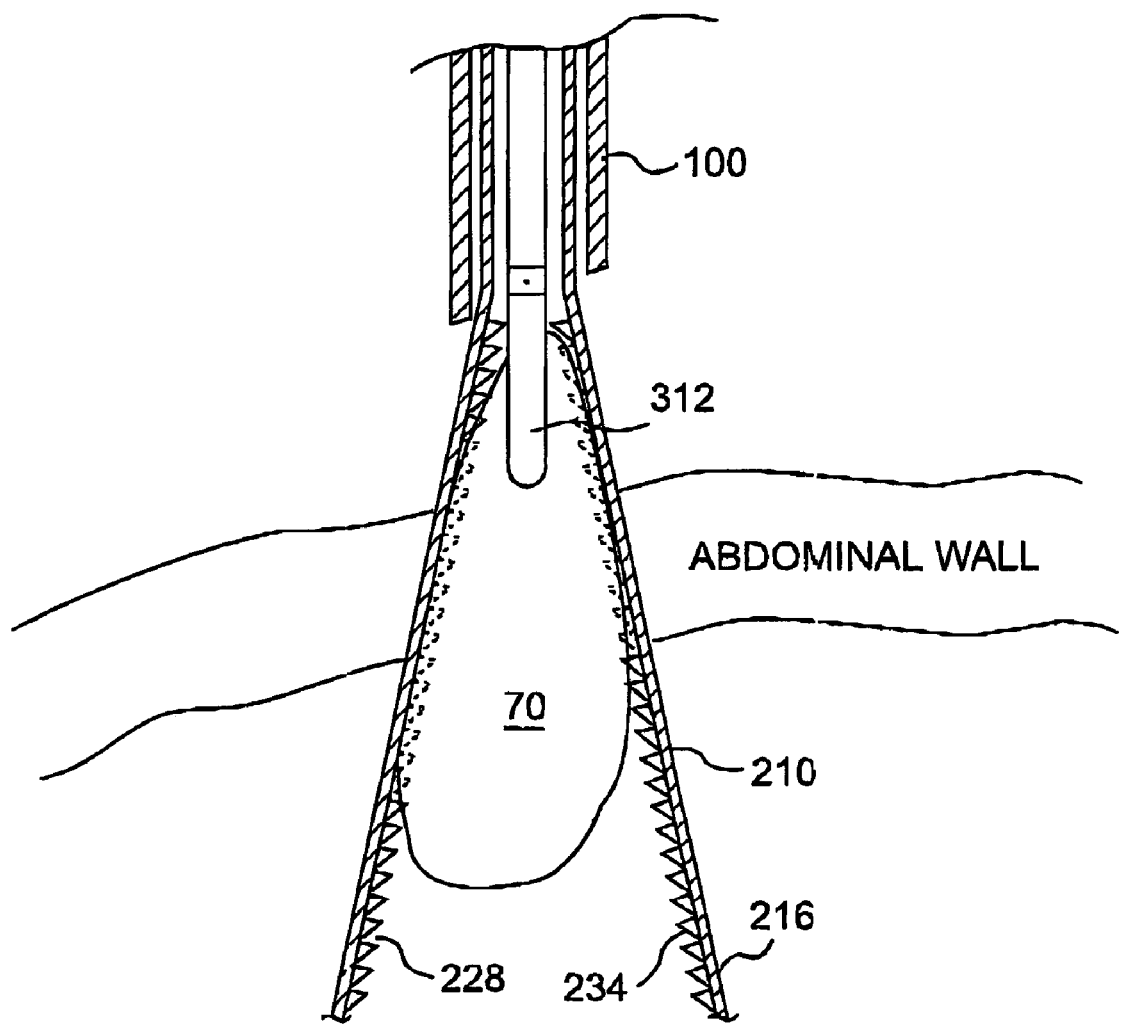
FIG. 11 is a side elevation view of a grasper and cannula with another embodiment of a dilator extractor of the present invention having tissue-engaging protrusions being withdrawn from the abdominal cavity with the tissue specimen.

FIG. 11 shows an alternate embodiment inner surface 228 of conical section 216 which is equipped with tissue retaining protrusions such as teeth 234. Preferably, teeth 234 are generally pointed toward trailing end 206 when dilator 210 is in the expanded position so that as dilator 210 closes around the tissue as shown in FIG. 11, teeth 234 bite into the tissue, thus supplying the dominance of the counter acting force to the extraction force rather than the friction of the tissue against inner surface 228 of conical section 216. It will be appreciated by those skilled in the art that teeth 234 may also be included on the surface of shank 250 if so desired.

It will be appreciated by those skilled in the art that other forms of tissue retaining protrusions are suitable for gripping the tissue, for example, tabs, ridges, and knurling. Additionally, the tissue retaining protrusions are preferably uniformly spaced around the longitudinal axis of dilator extractor 200 to provide an even distribution of retaining force against the tissue. Alternatively, tissue retaining protrusions may be positioned on only one side if so desired. Tissue retaining protrusions may also be spaced substantially about the entire area of inner surface 228 of conical section 216. Preferably, the tissue retaining protrusions are adapted to grab the tissue without penetrating it in order to reduce the risk of content spillage from the tissue.

Having described the apparatus, methods for its use will now be described. It should be understood that the order disclosed is only preferred and that the steps may be performed in other orders while still being within the scope of the present invention. Additionally, some steps may be repeated as necessary or omitted.

A preferred method for preparing the dilator extractor for surgical use includes producing body 202 and dilator 210. Body 202 and dilator 210 may be of the same material with a different thickness. Shank 250 is then attached to body 202. Once dilator 210 and body 202 are assembled together, a key is used to engage distal end 260 of shank 250 to wind dilator around the mid-longitudinal axis of dilator extractor 200. Once dilator 210 is sufficiently wound, for example, in a substantially cylindrical shape, retainer 218 is put onto or wrapped around dilator 210 to retain dilator 210 in an unexpanded position. The key is removed from distal end A preferred method of removing tissue from the abdominal cavity is shown in FIGS. 8–10. Cannula 100 is inserted through the abdominal wall and into cavity 60, which is preferably pressurized. A cannula having a maximum diameter preferably in the range of 3 mm to 5 mm is used in order to make the procedure less invasive. Dilator extractor 200 is inserted into cannula 100 through seal 102 to a position where leading end 211 of dilator 210 extends beyond leading end 104 of cannula 100. Dilator 210 is expanded to form tissue extraction space 214. Grasper 300 is inserted into dilator extractor 200 through a pair of seals and through lumen 208. Shank 250 is bent by the insertion of grasper 300 as shown in FIG. 8 such that grasper 300 extends generally through the center of conical section 216 of dilator 210. A portion of grasper 300 interacts with shank 250 to cause shank 250 to move away from the mid-longitudinal axis of dilator extractor 200. The interaction of grasper 300 with shank 250 may occur while grasper 300 is being inserted through dilator extractor 200 in a direction substantially parallel to the mid-longitudinal axis of dilator extractor 200. The tissue is grasped by grasper 300 and manipulated into tissue space 214. If desired, grasper 300 may be locked to dilator extractor 200 to provide more stability. Next, an upward force is exerted on dilator extractor 200, dilating the trocar wound such that the tissue is removed from the cavity under the influence of the upward force. The upward force also causes conical section 216 to roll-up, creating a generally evenly distributed constricting force upon the captured tissue. The constricting force greatly reduces the risk of the tissue tearing or rupturing at the grasper/tissue interface.

Alternately, for tissue containing a fluid such as bile in a gallbladder, additional steps may be included such as suctioning out the fluid prior to the extraction step. For example, a needle of a syringe device is inserted into grasper 300 through the seals and through the lumen to a position where the leading end of the needle extends beyond leading end 204 of body 202 of dilator extractor 200. Fluid is then suctioned from the tissue through the needle by the syringe. It will be appreciated that vacuum sources other than the syringe may be used to aspirate the tissue, for example, an aspirator. It will be further appreciated that aspiration may occur during other phases of the operation prior to the extraction of the tissue from the wound site. For example, a needle may be inserted through lumen 208 of dilator extractor 200 and fluid suctioned from the tissue before grasper 300 is inserted or used.

To further reduce the extraction force needed to withdraw the assembly with the tissue, the tissue may be treated to at least partially dissolve the tissue or its contents, for example, gallstones of a gallbladder. A syringe may be used to inject a composition capable of dissolving tissue. One example of such a composition is methyl tert-butyl ether. The tissue is treated preferably after fluid is suctioned. It will be appreciated that the tissue may be treated irrespective of any fluid suction.

Simulated dilator extractors were built and tested in the abdominal cavity of a swine. Aluminum cones of varying base diameters representing varying tissue sizes simulated the dilator section. Abdominal access for the cones was gained through a 100 mm incision along the midline of the animal. A 5 mm trocar with a single sided cutting tip obturator (rather than the more common three side pyramidal tip) was used to entry the cavity through a circular 5 mm wound located approximately 30 mm to the left of the midline. Each of four simulators consisting of 5 mm cylinders, 100 mm long transitioning into truncated cones with 5 mm diameter tops tapering to bases of 15, 20, 25, 30 mm diameters respectively, were separately tested by inserting them through the access incision. The 5 mm trocar was then inserted into the abdominal cavity, the obturator removed, and the 5 mm simulator tops were then inserted from the distal of the cannula so that they were exposed above the cannula valve. A force gage was then attached to the exposed section. The vertical pull force required to dilate the 5 mm puncture wound so that the cone was total extracted from the animal was then measured with a calibrated force gage. A new 5 mm trocar site was used for each of the four cones. The extraction force is shown in the table below:

| Cone Base Diameter, mm | Upward Extraction Force, lbs |
|---|---|
| 15 | 12 |
| 20 | 21 |
| 25 | 37 |
| 30 | 50 |

Each measurement was repeated using the same puncture wound to test the extent to which the wound had been torn or permanently stretched. The data indicated that dilation of 2 to 3 times is possible. In ranges up to 20–25 mm, the forces are of reasonable magnitude to make the device practical. Minimizing wound size is important to minimizing postoperative hernias and other complications.

Figure 7A:
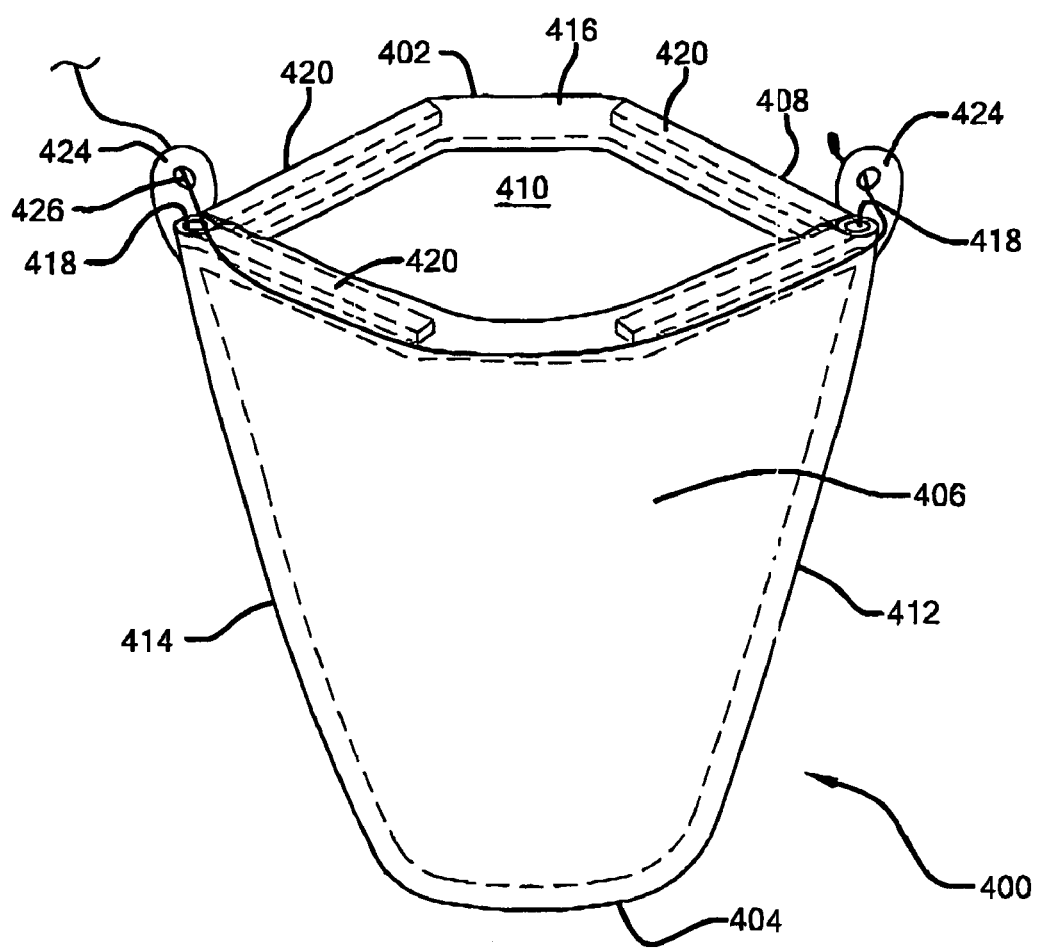
FIG. 7A is a perspective view of a tissue collection bag with extension arms in accordance with another preferred embodiment of the present invention.
Figure 7B:
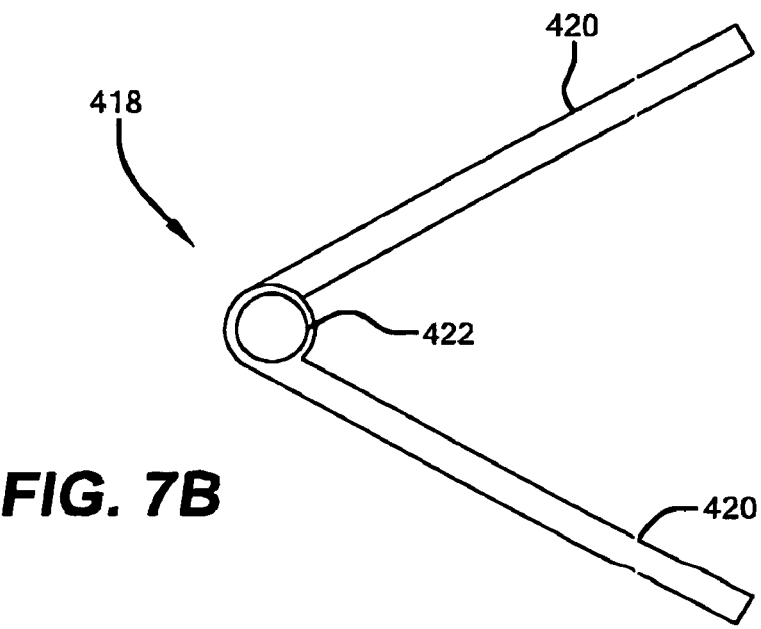
FIG. 7B is a top view of one of the extension arms of FIG. 7A.

FIG. 7A shows a tissue collection bag in accordance with another preferred embodiment of the present invention generally referred to by the number 400. Bag 400 includes a top 402, a bottom 404, a first side 406, a second side 408 and an interior 410. First and second sides 406, 408 are preferably heat welded together along interface 412, 414. Bag 400 is preferably made of a flexible material such as polyurethane. Top 402 includes a hem 416. Hem 416 is preferably heat-sealed and configured to receive an expansion member 418 at each juncture of first and second sides 406, 408.

Expansion member 418 includes a bend preferably in the form of a torsion coil with an arm 420 at each end of coil 422. Coil 422 preferably has between one to four turns, though the invention is not so limited. In a deployed position, arms 420 have an included angle therebetween of approximately 120 degrees. As will be appreciated by others of ordinary skill in the art, arms 420 may be biased to open at other angles greater or less than 120 degrees, such as 45 degrees or 90 degrees. Expansion member 418 may also have more than two arms, for example, a third arm depending downwardly towards bottom 404 of bag 400. The bend and any arms associated therewith may be made of a shape memory material.

Preferably an eyelet 424 is formed on the top of expansion member 418. Eyelet 424 is configured for grasping by an instrument such as grasper 300. Eyelet 424 preferably has an opening 426 to permit a thread or wire to be inserted therethrough to aid in closing bag 400. The thread may extend within hem 416 and through eyelet 424, through only eyelet 424, or through hem 416 alone. Other features for closing bag 400 may be used, for example, a press-seal such as found on sandwich bags.

In use, bag 400 is inserted through a cannula in an undeployed position with a retainer wrapped therearound in a generally cylindrical configuration in a similar fashion to dilator extractor 200. Once inserted into the cavity of the patient, bag 400 is deployed and expansion arms 420 are released to open top 402 of bag 400. A grasper is used to manipulate tissue into bag 400. Once the tissue is inside bag 400, the eyelets are held by a grasper and the bag extracted from the cavity. Before extracting bag 400 from the cavity, a thread or wire may be inserted through opening 426 of each eyelet and pulled to provide a better seal of top 402.

Bag 400 may be inserted and deployed without any attached link such as a handle or wire remaining outside the cavity. Such a configuration is advantageous when used in combination with a dilator extractor as the dilator extractor may be used to withdraw a relatively large tissue specimen through a small incision with little risk of leakage. Bag 400 may be shaped to have a generally conical cross section when deployed for ease of extraction via dilator extractor 200.

Other embodiments of the invention will be apparent to those skilled in the art from consideration of the specification and practice of the invention disclosed herein. For example only, the guide surface may also be configured to align the dilator cone with the mid-longitudinal axis of the dilator extractor when an instrument is inserted into the dilator extractor. It is intended that the specification and examples be considered as exemplary only.

We claim:

1. An extractor for removing tissue from an animal or human body cavity, said extractor comprising:
    a body having a leading end, a trailing end, and a lumen between said leading and trailing ends;
    a mid-longitudinal axis passing through said lumen of said body;
    a dilator at said leading end of said body being movable between an unexpanded position and an expanded position, said dilator having a single leaf adapted to be rolled at least in part around the mid-longitudinal axis of said extractor; and
    a guide surface configured to engage an instrument inserted through said lumen, said guide surface being adapted to move at least a portion of said dilator away from the mid-longitudinal axis of said extractor upon engagement with the instrument, said guide surface having a portion overlying a junction between said body and said dilator.

2. The extractor of claim 1, wherein said guide surface overlies at least one of said body and said dilator.

3. The extractor of claim 1, wherein said dilator includes a shank attached thereto, said shank having at least a portion of said guide surface formed thereon, said guide surface including a surface deviation being adapted to engage the instrument.

4. The extractor of claim 3, wherein said shank is welded to said dilator.

5. The extractor of claim 3, wherein said shank is attached to a portion of said body.

6. The extractor of claim 3, wherein said shank includes a key-way adapted to engage with a key to roll said leaf at least in part around the mid-longitudinal axis of said extractor.

7. The extractor of claim 1, wherein said dilator includes an interior portion, said guide surface including a surface deviation formed on said interior portion of said dilator.

8. The extractor of claim 1, wherein said leaf is metallic.

9. The extractor of claim 1, wherein said leaf is biased at least in part towards the expanded position.

10. An extractor for removing tissue from an animal or human body cavity, said extractor comprising:
- a body having a leading end, a trailing end, a lumen between said leading and trailing ends, and a depth stop;
- a mid-longitudinal axis passing through said lumen of said body;
- a dilator at said leading end of said body being movable between an unexpanded position and an expanded position;
- a collar having an opening and being movable relative to said body along the mid-longitudinal axis of said extractor, said body being adapted to pass through said opening in said collar; and
- a retainer attached to said collar, said retainer being adapted to retain said dilator in the unexpanded position until said depth stop contacts said collar and said body passes through said opening in said collar to move the dilator towards the expanded position.

11. The extractor of claim 10, wherein said depth stop has a shoulder adapted to contact a proximal portion of said collar.

12. The extractor of claim 11, wherein said body has a length from said depth stop to said dilator, and said collar and said retainer have a combined length along a central longitudinal axis coaxial with said opening of said collar, the length from said depth stop to said dilator being approximately the same as the combined length of said collar and said retainer.

13. A method for removing tissue from an animal or human body cavity, the method comprising the steps of:
- providing an extractor having a dilator movable between an unexpanded position and an expanded position, the dilator being made of a material that is biased at least in part toward the expanded position, the extractor having an interior surface with a surface deviation;
- inserting the extractor through a cannula and at least in part into the body cavity;
- releasing the dilator to move at least in part toward the expanded position;
- engaging the surface deviation of the extractor with an instrument to further move the dilator toward the expanded position; and
- removing tissue from the body cavity.

14. The method of claim 13, further comprising the step of engaging the tissue with the instrument, the step of engaging the portion of the extractor being performed before the step of engaging the tissue.

15. The method of claim 13, wherein the extractor has a mid-longitudinal axis, the step of engaging including moving the instrument substantially parallel to the mid-longitudinal axis of the extractor to engage the extractor to further move the dilator toward the expanded position.

16. An extractor for removing tissue from an animal or human body cavity, said extractor comprising:
- a body having a leading end, a trailing end, and a lumen between said leading and trailing ends;
- a mid-longitudinal axis passing through said lumen of said body;
- a dilator at said leading end of said body being movable between an unexpanded position and an expanded position, said dilator having a single leaf adapted to be roiled at least in part around the mid-longitudinal axis of said extractor; and
- a guide surface configured to engage an instrument inserted through said lumen, said guide surface being adapted to move at least a portion of said dilator away from the mid-longitudinal axis of said extractor upon engagement with the instrument, said dilator including a shank attached thereto, said shank having at least a portion of said guide surface formed thereon, said guide surface including a surface deviation being adapted to engage the instrument.

17. The extractor of claim 16, wherein said shank is welded to said dilator.

18. The extractor of claim 16, wherein said shank is attached to a portion of said body.

19. The extractor of claim 16, wherein said shank includes a key-way adapted to engage with a key to roll said leaf at least in part around the mid-longitudinal axis of said extractor.

20. The extractor of claim 16, wherein said leaf is metalic.

21. The extractor of claim 16, wherein said leaf is biased at least in part towards the expanded position.

* * * * *

UNITED STATES PATENT AND TRADEMARK OFFICE
CERTIFICATE OF CORRECTION

| | |
|---|---|
| PATENT NO. | : 7,041,055 B2 |
| APPLICATION NO. | : 10/680973 |
| DATED | : May 9, 2006 |
| INVENTOR(S) | : Wayne P. Young et al. |

It is certified that error appears in the above-identified patent and that said Letters Patent is hereby corrected as shown below:

Column 14:
Line 19: change "roiled" to -- rolled --; and
Line 38: change "metalic" to -- metallic --.

Signed and Sealed this

Twenty-second Day of August, 2006

JON W. DUDAS
*Director of the United States Patent and Trademark Office*